US010017555B2

(12) United States Patent
Zhou et al.

(10) Patent No.: US 10,017,555 B2
(45) Date of Patent: Jul. 10, 2018

(54) LONG-ACTING BLOOD SUGAR DECREASING FUSION PROTEIN

(71) Applicant: Genor Biopharma Co., Ltd., Shanghai (CN)

(72) Inventors: Joe Zhou, Shanghai (CN); Qing Zhou, Shanghai (CN); Rulei Chen, Shanghai (CN); Shu Shi, Shanghai (CN); Weihong Nian, Shanghai (CN); Hongbin Yan, Shanghai (CN)

(73) Assignee: Genor Biopharma Co., Ltd, Shanghai (CN)

( * ) Notice: Subject to any disclaimer, the term of this patent is extended or adjusted under 35 U.S.C. 154(b) by 28 days.

(21) Appl. No.: 14/898,698

(22) PCT Filed: Jul. 2, 2014

(86) PCT No.: PCT/CN2014/081490
§ 371 (c)(1),
(2) Date: Dec. 15, 2015

(87) PCT Pub. No.: WO2015/000413
PCT Pub. Date: Jan. 8, 2015

(65) Prior Publication Data
US 2016/0222079 A1    Aug. 4, 2016

(30) Foreign Application Priority Data
Jul. 4, 2013  (CN) .......................... 2013 1 0280199

(51) Int. Cl.
*A61K 38/26* (2006.01)
*A61K 39/00* (2006.01)
*C07K 14/605* (2006.01)
*A61K 38/00* (2006.01)

(52) U.S. Cl.
CPC ............ *C07K 14/605* (2013.01); *A61K 38/26* (2013.01); *A61K 38/00* (2013.01); *C07K 2319/00* (2013.01); *C07K 2319/30* (2013.01)

(58) Field of Classification Search
CPC .............................. C07K 14/605; A61K 38/26
See application file for complete search history.

(56) References Cited

U.S. PATENT DOCUMENTS

| 7,271,149 B2 | 9/2007 | Glaesner et al. | |
| 8,496,935 B2 | 7/2013 | Karrer et al. | |
| 2004/0053370 A1* | 3/2004 | Glaesner ................ | C07H 21/04 435/69.7 |

FOREIGN PATENT DOCUMENTS

| CN | 1483041 A | 3/2004 |
| CN | 101910199 A | 12/2010 |
| CN | 101998965 A | 3/2011 |
| WO | WO 2009/086320 A1 | 7/2009 |
| WO | WO 2011/056713 A2 | 5/2011 |

OTHER PUBLICATIONS

Anagnostis et al. (Apr. 2011) "Glucagon-like peptide-1-based therapies and cardiovascular disease: looking beyond glycaemic control," Diabetes Obes. Metab. 13:302-312.
Aronoff et al. (2004) "Glucose Metabolism and Regulation: Beyond Insulin and Glucagon," Diabetes Spectrum. 17:183-190.
Baggio et al. (2004) "A recombinant human glucagon-like peptide (GLP)-1-albumin protein (albugon) mimics peptidergic activation of GLP-1 receptor-dependent pathways coupled with satiety, gastrointestinal motility, and glucose homeostasis," Diabetes. 53:2492-2500.
Baggio et al. (2007) "Biology of incretins: GLP-1 and GIP," Gastroenterology. 132:2131-2157.
Bao et al. (Aug. 26, 2011) "Albiglutide, a long lasting glucagon-like peptide-1 analog, protects the rat heart against ischemia/reperfusion injury: evidence for improving cardiac metabolic efficiency," PLoS ONE. 6(8):e23570.
Bolli et al. (2008) "Efficacy and tolerability of vildagliptin vs. pioglitazone when added to metformin: a 24-week, randomized, double-blind study," Diabetes Obes Metab. 10:82-90.
Ding et al. (Mar. 25, 2011) "Glucagon-like peptide 1 stimulates post-translational activation of glucokinase in pancreatic beta cells," J. Biol. Chem. 286(19):16768-16774.
Drucker (2003) "Enhancing incretin action for the treatment of type 2 diabetes," Diabetes Care. 26:2929-2940.
Drucker et al. (2006) "The incretin system: glucagon-like peptide-1 receptor agonists and dipeptidyl peptidase-4 inhibitors in type 2 diabetes," Lancet. 368:1696-1705.
Eng et al. (1992) "Isolation and characterization of exendin-4, an exendin-3 analogue, from Heloderma suspectum venom. Further evidence for an exendin receptor on dispersed acini from guinea pig pancreas," J. Biol. Chem. 267:7402-7405.
Farilla et al. (2003) "Glucagon-like peptide 1 inhibits cell apoptosis and improves glucose responsiveness of freshly isolated human islets," Endocrinology. 144:5149-5158.
Glaesner et al. (2010) "Engineering and characterization of the long-acting glucagon-like peptide-1 analogue LY2189265, an Fc fusion protein," Diabetes Metab Res Rev. 26:287-296.
International Search Report with Written Opinion corresponding to International Patent Application No. PCT/CN2014/081490, dated Sep. 22, 2014.

(Continued)

*Primary Examiner* — Gyan Chandra
(74) *Attorney, Agent, or Firm* — Leydig, Voit & Mayer, Ltd.

(57) ABSTRACT

The present invention provides an anthropogenic glucagon-like peptide-1 (GLP-1) recombinant protein molecule fused with an anthropogenic immunoglobulin subtype (IgG2) Fc section and a preparation method and purpose thereof. The fusion protein has the biological activity of GLP-1, and also has a significantly prolonged half-life in vivo. The fusion protein can be used to treat type II diabetes, obesity, and other diseases that are treated by decreasing serum glucose, suppressing gastrointestinal motility, and emptying or suppressing food intake.

14 Claims, 6 Drawing Sheets

(56) References Cited

OTHER PUBLICATIONS

Junttila et al. (2010) "Superior in vivo efficacy of afucosylated trastuzumab in the treatment of HER2-amplified breast cancer," Cancer Res. 70(11):4481-4489.

Klonoff et al. (2008) "Exenatide effects on diabetes, obesity, cardiovascular risk factors and hepatic biomarkers in patients with type 2 diabetes treated for at least 3 years," Curr. Med. Res. Opin. 24:275-286.

Lund et al. (1982) "Pancreatic preproglucagon cDNA contains two glucagon-related coding sequences arranged in tandem," Proc. Natl. Acad. Sci. USA. 79(2):345-349.

MacDonald et al. (2002) "The Multiple Actions of GLP-1 on the Process of Glucose-Stimulated Insulin Secretion," Diabetes. 51:S434-S442.

Moller (2001) "New drug targets for type 2 diabetes and the metabolic syndrome," Nature. 414:821-827.

Nathan et al. (2009) "Medical management of hyperglycemia in type 2 diabetes: a consensus algorithm for the initiation and adjustment of therapy: a consensus statement of the American Diabetes Association and the European Association for the Study of Diabetes," Diabetes Care. 32:193-203.

Nauck et al. (1986) "Reduced incretin effect in type 2 (non-insulin-dependent) diabetes," Diabetologia. 29:46-52.

Nauck et al. (1993) "Normalization of fasting hyperglycaemia by exogenous glucagon-like peptide 1 (7-36 amide) in type 2 (non-insulin-dependent) diabetic patients," Diabetologia. 36:741-744.

Nauck et al. (1993) "Preserved incretin activity of glucagon-like peptide 1 [7-36 amide] but not of synthetic human gastric inhibitory polypeptide in patients with type-2 diabetes mellitus," J. Clin. Invest. 91:301-307.

Nauck et al. (1996) "Effects of subcutaneous glucagon-like peptide 1 (GLP-1 [7-36 amide]) in patients with NIDDM," Diabetologia. 39:1546-1553.

Nauck et al. (1998) "Influence of glucagon-like peptide 1 on fasting glycemia in type 2 diabetic patients treated with insulin after sulfonylurea secondary failure," Diabetes Care. 21:1925-1931.

Parkes et al. (2001) "Pharmacokinetic actions of exendin-4 in the rat: Comparison with glucagon-like peptide-1," Drug Dev. Res. 53:260-267.

Salfeld (2007) "Isotype selection in antibody engineering," Nature Biotechnology. 25(12):1369-1372.

Schwartz et al. (2008) "Effect of exenatide on 24-hour blood glucose profile compared with placebo in patients with type 2 diabetes: a randomized, double-blind, two-arm, parallel-group, placebo-controlled, 2-week study," Clin. Ther. 30:858-867.

Shields et al. (2001) "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 276(9):6591-6604.

Toft-Nielsen et al. (2001) "Determinants of the impaired secretion of glucagon-like peptide-1 in type 2 diabetic patients," J. Clin. Endocrinol. Metab. 86:3717-3723.

Vella et al. (2007) "Effects of dipeptidyl peptidase-4 inhibition on gastrointestinal function, meal appearance, and glucose metabolism in type 2 diabetes," Diabetes. 56:1475-1480.

Wang et al. (2004) "Biological activity of bevacizumab, a humanized anti-VEGF antibody in vitro," Angiogenesis. 7:335-345.

Wang et al. (2010) "Novel GLP-1 fusion chimera as potent long acting GLP-1 receptor agonist," PLoS ONE. 5(9):e12734.

Zander et al. (2002) "Effect of 6-week course of glucagon-like peptide 1 on glycaemic control, insulin sensitivity, and beta-cell function in type 2 diabetes: a parallel-group study," Lancet. 359:824-830.

Knudsen et al., "*Potent Derivatives of Glucagon-like Peptide-1 with Pharmacokinetic Properties Suitable for Once Daily Administration*", J. Med. Chem., 2000, 43: 1664-1669.

\* cited by examiner

SEQUENCE LISTING

```
<160> NUMBER OF SEQ ID NOS: 13

<210> SEQ ID NO 1
<211> LENGTH: 864
<212> TYPE: DNA
<213> ORGANISM: Artificial sequence
<220> FEATURE:
<223> OTHER INFORMATION: synthetic construct

<400> SEQUENCE: 1
atggagttgg gactgtcttg gattttcctg ttggctattc tgaaaggtgt gcaatgtcac      60
```

```
ggcgagggca ccttcacctc cgacgtgtcc tcctatctcg aggagcaggc cgccaaggag    120
ttcatcgcct ggctggtgaa gggcggcggc ggtggtggtg gctccggagg cggcggctct    180
ggtggcggtg gcagcgtcga gtgcccaccg tgcccagcac cacctgtggc aggaccgtca    240
gtcttcctct cccccccaaa acccaaggac accctcatga tctcccggac ccctgaggtc    300
acgtgcgtgg tggtggacgt gagccacgaa gaccccgagg tccagttcaa ctggtacgtg    360
gacggcgtgg aggtgcataa tgccaagaca aagccacggg aggagcagtt caacagcacg    420
ttccgtgtgg tcagcgtcct caccgtcgtg caccaggact ggctgaacgg caaggagtac    480
aagtgcgcgg tctccaacaa aggcctccca gcccccatcg agaaaaccat ctccaaaacc    540
aaagggcagc cccgagaacc acaggtgtac accctgcccc catcccggga ggagatgacc    600
aagaaccagg tcagcctgac ctgcctggtc aaaggcttct accccagcga catcgccgtg    660
gagtgggaga gcaatgggca gccggagaac aactacaaga ccacgcctcc catgctggac    720
tccgacggct ccttcttcct ctacagcaag ctcaccgtgg acaagagcag gtggcagcag    780
gggaacgtct tctcatgctc cgtgatgcat gaggctctgc acaaccacta cacgcagaag    840
agcctctccc tgtctccggg taaa                                           864

<210> SEQ ID NO 2
<211> LENGTH: 876
<212> TYPE: DNA
<213> ORGANISM: Artificial sequence
<220> FEATURE:
<223> OTHER INFORMATION: synthetic construct

<400> SEQUENCE: 2
atggagttgg gactgtcttg gattttcctg ttggctattc tgaaaggtgt gcaatgtcac     60
ggcgagggca ccttcacctc cgacgtgtcc tcctatctcg aggagcaggc cgccaaggag    120
ttcatcgcct ggctggtgaa gggcggcggc ggtggtggtg gctccggagg cggcggctct    180
ggtggcggtg gcagcgagcg caaatgttgt gtcgagtgcc caccgtgccc agcaccacct    240
gtggcaggac cgtcagtctt cctcttcccc ccaaaaccca aggacaccct catgatctcc    300
cggacccctg aggtcacgtg cgtggtggtg gacgtgagcc acgaagaccc cgaggtccag    360
ttcaactggt acgtggacgg cgtggaggtg cataatgcca agacaaagcc acgggaggag    420
cagttcaaca gcacgttccg tgtggtcagc gtcctcaccg tcgtgcacca ggactggctg    480
aacggcaagg agtacaagtg caaggtctcc aacaaaggcc tcccagcccc catcgagaaa    540
accatctcca aaaccaaagg cagcccccga gaaccacagg tgtacaccct gcccccatcc    600
cgggaggaga tgaccaagaa ccaggtcagc ctgacctgcc tggtcaaagg cttctacccc    660
agcgacatcg ccgtggagtg ggagagcaat gggcagccgg agaacaacta caagaccacg    720
cctcccatgc tggactccga cggctccttc ttcctctaca gcaagctcac cgtggacaag    780
agcaggtggc agcaggggaa cgtcttctca tgctccgtga tgcatgaggc tctgcacaac    840
cactacacgc agaagagcct ctccctgtct ccgggt                              876

<210> SEQ ID NO 3
<211> LENGTH: 861
<212> TYPE: DNA
<213> ORGANISM: Artificial sequence
<220> FEATURE:
<223> OTHER INFORMATION: synthetic construct

<400> SEQUENCE: 3
atggagttgg gactgtcttg gattttcctg ttggctattc tgaaaggtgt gcaatgtcac     60
```

```
ggcgagggca ccttcacctc cgacgtgtcc tcctatctcg aggagcaggc cgccaaggag    120
ttcatcgcct ggctggtgaa gggcggcggc ggtggtggtg gctccggagg cggcggctct    180
ggtggcggtg gcagcgtcga gtgcccaccg tgcccagcac cacctgtggc aggaccgtca    240
gtcttcctct ccccccaaa acccaaggac accctcatga tctcccggac ccctgaggtc    300
acgtgcgtgg tggtggacgt gagccacgaa gaccccgagg tccagttcaa ctggtacgtg    360
gacggcgtgg aggtgcataa tgccaagaca aagccacggg aggagcagtt caacagcacg    420
ttccgtgtgg tcagcgtcct caccgtcgtg caccaggact ggctgaacgg caaggagtac    480
aagtgcaagg tctccaacaa aggcctccca gcccccatcg agaaaaccat ctccaaaacc    540
aaagggcagc cccgagaacc acaggtgtac accctgcccc catcccggga ggagatgacc    600
aagaaccagg tcagcctgac ctgcctggtc aaaggcttct accccagcga catcgccgtg    660
gagtgggaga gcaatgggca gccggagaac aactacaaga ccacgcctcc catgctggac    720
tccgacggct ccttcttcct ctacagcaag ctcaccgtgg acaagagcag gtggcagcag    780
gggaacgtct tctcatgctc cgtgatgcat gaggctctgc acaaccacta cacgcagaag    840
agcctctccc tgtctccggg t                                              861

<210> SEQ ID NO 4
<211> LENGTH: 288
<212> TYPE: PRT
<213> ORGANISM: Artificial sequence
<220> FEATURE:
<223> OTHER INFORMATION: synthetic construct

<400> SEQUENCE: 4

Met Glu Leu Gly Leu Ser Trp Ile Phe Leu Leu Ala Ile Leu Lys Gly
1               5                   10                  15

Val Gln Cys His Gly Glu Gly Thr Phe Thr Ser Asp Val Ser Ser Tyr
            20                  25                  30

Leu Glu Glu Gln Ala Ala Lys Glu Phe Ile Ala Trp Leu Val Lys Gly
        35                  40                  45

Gly Gly Gly Gly Gly Ser Gly Gly Gly Gly Ser Gly Gly Gly Gly
    50                  55                  60

Ser Val Glu Cys Pro Pro Cys Pro Ala Pro Pro Val Ala Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Phe Arg Val Val
    130                 135                 140

Ser Val Leu Thr Val Val His Gln Asp Trp Leu Asn Gly Lys Glu Tyr
145                 150                 155                 160

Lys Cys Ala Val Ser Asn Lys Gly Leu Pro Ala Pro Ile Glu Lys Thr
                165                 170                 175

Ile Ser Lys Thr Lys Gly Gln Pro Arg Glu Pro Gln Val Tyr Thr Leu
            180                 185                 190

Pro Pro Ser Arg Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
```

210                 215                 220
Asn Gly Gln Pro Glu Asn Asn Tyr Lys Thr Thr Pro Pro Met Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285

<210> SEQ ID NO 5
<211> LENGTH: 292
<212> TYPE: PRT
<213> ORGANISM: Artificial sequence
<220> FEATURE:
<223> OTHER INFORMATION: synthetic construct

<400> SEQUENCE: 5

Met Glu Leu Gly Leu Ser Trp Ile Phe Leu Leu Ala Ile Leu Lys Gly
1               5                   10                  15

Val Gln Cys His Gly Glu Gly Thr Phe Thr Ser Asp Val Ser Ser Tyr
            20                  25                  30

Leu Glu Glu Gln Ala Ala Lys Glu Phe Ile Ala Trp Leu Val Lys Gly
        35                  40                  45

Gly Gly Gly Gly Gly Ser Gly Gly Gly Ser Gly Gly Gly Gly Gly Gly
    50                  55                  60

Ser Glu Arg Lys Cys Cys Val Glu Cys Pro Pro Cys Pro Ala Pro Pro
65                  70                  75                  80

Val Ala Gly Pro Ser Val Phe Leu Phe Pro Pro Lys Pro Lys Asp Thr
                85                  90                  95

Leu Met Ile Ser Arg Thr Pro Glu Val Thr Cys Val Val Val Asp Val
            100                 105                 110

Ser His Glu Asp Pro Glu Val Gln Phe Asn Trp Tyr Val Asp Gly Val
        115                 120                 125

Glu Val His Asn Ala Lys Thr Lys Pro Arg Glu Glu Gln Phe Asn Ser
    130                 135                 140

Thr Phe Arg Val Val Ser Val Leu Thr Val Val His Gln Asp Trp Leu
145                 150                 155                 160

Asn Gly Lys Glu Tyr Lys Cys Lys Val Ser Asn Lys Gly Leu Pro Ala
                165                 170                 175

Pro Ile Glu Lys Thr Ile Ser Lys Thr Lys Gly Gln Pro Arg Glu Pro
            180                 185                 190

Gln Val Tyr Thr Leu Pro Pro Ser Arg Glu Glu Met Thr Lys Asn Gln
        195                 200                 205

Val Ser Leu Thr Cys Leu Val Lys Gly Phe Tyr Pro Ser Asp Ile Ala
    210                 215                 220

Val Glu Trp Glu Ser Asn Gly Gln Pro Glu Asn Asn Tyr Lys Thr Thr
225                 230                 235                 240

Pro Pro Met Leu Asp Ser Asp Gly Ser Phe Phe Leu Tyr Ser Lys Leu
                245                 250                 255

Thr Val Asp Lys Ser Arg Trp Gln Gln Gly Asn Val Phe Ser Cys Ser
            260                 265                 270

Val Met His Glu Ala Leu His Asn His Tyr Thr Gln Lys Ser Leu Ser
        275                 280                 285

Leu Ser Pro Gly

<210> SEQ ID NO 6
<211> LENGTH: 287
<212> TYPE: PRT
<213> ORGANISM: Artificial sequence
<220> FEATURE:
<223> OTHER INFORMATION: synthetic construct

<400> SEQUENCE: 6

Met Glu Leu Gly Leu Ser Trp Ile Phe Leu Leu Ala Ile Leu Lys Gly
1               5                   10                  15

Val Gln Cys His Gly Glu Gly Thr Phe Thr Ser Asp Val Ser Ser Tyr
            20                  25                  30

Leu Glu Glu Gln Ala Ala Lys Glu Phe Ile Ala Trp Leu Val Lys Gly
        35                  40                  45

Gly Gly Gly Gly Gly Ser Gly Gly Gly Ser Gly Gly Gly Gly
    50                  55                  60

Ser Val Glu Cys Pro Pro Cys Pro Ala Pro Pro Val Ala Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Asp Val Ser His Glu Asp Pro
            100                 105                 110

Glu Val Gln Phe Asn Trp Tyr Val Asp Gly Val Glu Val His Asn Ala
        115                 120                 125

Lys Thr Lys Pro Arg Glu Glu Gln Phe Asn Ser Thr Phe Arg Val Val
    130                 135                 140

Ser Val Leu Thr Val Val His Gln Asp Trp Leu Asn Gly Lys Glu Tyr
145                 150                 155                 160

Lys Cys Lys Val Ser Asn Lys Gly Leu Pro Ala Pro Ile Glu Lys Thr
                165                 170                 175

Ile Ser Lys Thr Lys Gly Gln Pro Arg Glu Pro Gln Val Tyr Thr Leu
            180                 185                 190

Pro Pro Ser Arg Glu Glu Met Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Met Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly
        275                 280                 285

<210> SEQ ID NO 7
<211> LENGTH: 34
<212> TYPE: DNA
<213> ORGANISM: Artificial sequence
<220> FEATURE:
<223> OTHER INFORMATION: synthetic construct

<400> SEQUENCE: 7
gcggccgcga attcatggag ttgggactgt cttg      34

-continued

<210> SEQ ID NO 8
<211> LENGTH: 36
<212> TYPE: DNA
<213> ORGANISM: Artificial sequence
<220> FEATURE:
<223> OTHER INFORMATION: synthetic construct

<400> SEQUENCE: 8
ccaccgccac cgtcgctcgc gtttacaaca cagctc        36

<210> SEQ ID NO 9
<211> LENGTH: 39
<212> TYPE: DNA
<213> ORGANISM: Artificial sequence
<220> FEATURE:
<223> OTHER INFORMATION: synthetic construct

<400> SEQUENCE: 9
ggtggcggtg gcagcgagcg caaatgttgt gtcgagtgc        39

<210> SEQ ID NO 10
<211> LENGTH: 35
<212> TYPE: DNA
<213> ORGANISM: Artificial sequence
<220> FEATURE:
<223> OTHER INFORMATION: synthetic construct

<400> SEQUENCE: 10
gtttaaacgg atcctcaacc cggagacagg gagag        35

<210> SEQ ID NO 11
<211> LENGTH: 15
<212> TYPE: PRT
<213> ORGANISM: Artificial sequence
<220> FEATURE:
<223> OTHER INFORMATION: synthetic construct

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 7
<212> TYPE: PRT
<213> ORGANISM: Artificial sequence
<220> FEATURE:
<223> OTHER INFORMATION: synthetic construct

<400> SEQUENCE: 12

Val Glu Cys Pro Pro Cys Pro
1               5

<210> SEQ ID NO 13
<211> LENGTH: 12
<212> TYPE: PRT
<213> ORGANISM: Artificial sequence
<220> FEATURE:
<223> OTHER INFORMATION: synthetic construct

<400> SEQUENCE: 13

Glu Arg Lys Cys Cys Val Glu Cys Pro Pro Cys Pro
1               5                   10

US 10,017,555 B2

LONG-ACTING BLOOD SUGAR DECREASING FUSION PROTEIN

CROSS-REFERENCE TO RELATED APPLICATIONS

This application is a U.S. National Stage Application filed under 35 U.S.C. § 371 of International Application No. PCT/CN2014/081490, filed Jul. 2, 2014, which claims the benefit of China Application No. 201310280199.3, filed Jul. 4, 2013. Both of these applications are hereby incorporated by reference in their entireties.

FIELD OF THE INVENTION

The present invention belongs to the field of biological pharmaceutics, particularly to the field of therapeutic biomacromolecule medicament. More particularly, the present invention discloses a fusion protein, and the preparation method and use thereof.

BACKGROUND OF THE INVENTION

Patients with type II diabetes (diabetes mellitus II, DM II, insulin resistant diabetes) account for 90-95% of all the patients with diabetes, and their amount increases by 6% annually. By 2025, the amount of the patients with type II diabetes is expected to reach 380 million across the world. Asia now is already the region with the most patients with diabetes. The amount of patients with diabetes in developing countries, such as China and India, increases most rapidly across the world. The latest large-scale epidemiological survey about diabetes in China was conducted in 2002 among 100,000 people according to the diagnostic criteria published by WHO in 1999, showing that the prevalence rates in people older than 18 years in urban and rural areas are 4.5% and 1.8%, respectively. In the past two decades, the prevalence rate of diabetes has a nearly 4-fold increase in China.

Currently, the major therapies for type II diabetes include insulin replacement therapy (insulin and insulin analogue) and oral administration of chemical hypoglycemics (insulin secretagogues which can directly stimulate insulin secretion, such as sulfonylureas and glinides; non-insulin secretagogues such as biguanides, thiazolidinediones and alpha glucosidase inhibitors, wherein the biguanides mainly reduce hepatic glucose output, the thiazolidinediones can improve insulin resistance, and the alpha glucosidase inhibitors mainly delay carbohydrate absorption in the intestines). Although the above-mentioned medicaments can decrease blood sugar, they may cause side effects such as hypoglycemia and weight gain, and progressive loss of the function of pancreatic beta-cells (Nature 2001, 414: 821-827).

GLP-1 (Glucagon-Like Peptide-1), as one of the incretins, simulates the "incretin effect" that decreases blood sugar under physiological conditions, and targets two major pathogenesis of diabetes (insufficient insulin secretion and insulin resistance) with unique therapeutic mechanism. At present, GLP-1 has been approved as the second-line medicament in developed countries (Diabetes Care. 2009, 32: 193-203).

GLP-1 promotes insulin secretion and inhibits glucagon secretion in a blood sugar concentration-dependent manner; that is, when blood sugar concentration is higher than normal level, GLP-1 produces an insulin secretion-promoting effect; and when blood sugar concentration is normal, this insulin secretion-promoting effect diminishes. Therefore, the treatment by exogenous GLP-1 will not induce hypoglycemia side effect due to overdose, which is the most prominent feature of GLP-1 analogues over other insulin secretagogues, as well as insulin and insulin analogues (Diabetologia. 1986, 29: 46-52; J Clin Invest. 1993, 91: 301-307; and J Clin Endocrinol Metab. 2001, 86: 3717-3723).

GLP-1 could control postprandial glucagon secretion by binding to the receptors on pancreatic alpha cells; promote proliferation of pancreatic beta cells, inhibit their apoptosis, and increase their sensitivity to glucose by interacting with pancreatic beta cells, thereby increasing glucose-dependent insulin secretion; reduce hepatic glycogen output by acting on liver; delay gastric emptying and reduce food intake by acting on stomach; and increase satiety and reduce appetite by acting on hypothalamus, thereby resulting in weight loss (Diabetes Care. 2003, 26: 2929-2940; Castroenterology. 2007, 132: 2131-2157; Proc Natl Acad Sci. 1982, 79(2): 345-349; Diabetologia. 1996, 39: 1546-1553; Endocrinology. 2003, 144: 5149-5158; Diabetes. 2002, 51: 5434-5442; Diabetologia. 1993, 36; 741-744; and Lancet. 2002, 359: 824-830).

In addition, GLP-1 may improve pathological defects in patients with type II diabetes, protects pancreatic beta cells and cardiovascular system, and has nerve protection effect. Therefore, GLP-1 can reduce occurrence of complications in patients with diabetes, and its advantages and comprehensive effects in decreasing blood sugar, losing weight, and protecting pancreatic cells and cardiovascular system, will certainly improve its position in the future treatment of type 11 diabetes (Diabetes Care. 1998, 21: 1925-1931; Diabetes Spectrum. 2004, 17: 183-190; Lancet. 2006, 368: 1696-1705; and PLoS ONE. 2011, 6(8): e23570).

Natural GLP-1 has no druggability, since it can be easily inactivated in vivo by endogenous DPP-4 (Dipeptidyl peptidase-4) that removes the N-terminal histidine (His) and alanine (Ala) residues of GLP-1, and has a half-life of less than 2 minutes. Therefore, the medicaments under development need to overcome this problem through various ways. At present, there are mainly two classes of GLP-1-targeting medicaments that are marketed or under development: one is small-molecule medicament that can inhibit the degradation effect of DPP-4 in vivo, the other is modified GLP-1 or GLP-1 analogue that has extended half-life without losing the biological function of GLP-1 (J Biol Chem. 1992, 267: 7402-7405; Drug Dev Res. 2001, 53: 260-267; Diabetes. 2007, 56: 1475-1480; Clin Ther. 2008, 30: 858-867; Diabetes Obes Metab. 2008, 10: 82-90; and Curr Med Res Opin. 2008, 24: 275-286).

GLP-1 analogues, GLP-1 mutants, GLP-1 long-acting formulations or DPP-4 inhibitors that have been successfully marketed or under development, are all originally developed to extend the in vivo half-life of active substances. At present, GLP-1 and most of analogues thereof developed at home and abroad possess similar therapeutic effects, and mainly differ in the action time and immunogenicity. Among those medicaments, the first marketed GLP-1 analogue, Exenatide, is developed by Eli Lilly and marketed in the United States in April, 2005, which is derived from the saliva of Gila monster (*Heloderma suspectum*) and needs to be administered twice a day by subcutaneous injection. The subsequently marketed Liraglutide, a human GLP-1 mutant developed by Novo Nordisk, is marketed in Europe in April, 2009 and in China in October, 2011, which needs to be administered once a day by subcutaneous injection. The human GLP-1 mutant that binds to a human immunoglobulin IgG Fc section, e.g., Dulaglutide under development by Eli Lilly, which takes advantage of the long circulating half-life of IgG and can be administered once a week, is the optimal one among current similar products (Diabetes Obes Metab. 2011, 13: 302-312).

The present invention relates to a fusion protein in which the amino acid sequence of positions 7 to 37 of a human GLP-1 is fused with a human IgG Fc section, which differs from Dulaglutide in that the human IgG Fc section used in this protein is IgG2 Fc section. From a safety perspective, it offers the following advantages:

1) The human GLP-1 polypeptide has low immunogenicity, and thus does not likely generate antibody during long-term use; and 2) The Fc section of certain IgG subtypes (such as IgG1) may bind to the Fc receptors on the surfaces of macrophages and NK cells, having ADCC (Antibody-Dependent Cell Cytotoxicity) and regulation effects. The Fc section of human IgG2 cannot bind to high-affinity Fc receptor, CD64, or to low-affinity Fc receptors, CD32 and CD16, and thus can reduce its ADCC effect.

In view of the above two advantages, the fusion protein of the present invention can not only reduce immunogenicity, but also avoid the effector function of the Fc section that is not associated with the GLP-1 treatment.

Neonatal Fc receptor (FcRn) can extend the half-life of IgG in blood, maintain a high level of IgG concentration in blood circulation, and keep the dynamic balance of antibody level. FcRn is expressed by vascular endothelial cells in normal adults, and can bind to IgG Fc section. Vascular endothelium is an important position where FcRn protects IgG from being degraded and metabolized. FcRn, which depends on endocytosis, not only absorbs IgG from the extracellular acidic environment, but also involves in IgG circulation and homeostatic regulation within cells. Under physiological conditions, when IgG concentration in serum is lower than normal level, more FcRns bind to Fc and decrease IgG degradation, such that IgG concentration can be maintained, when IgG concentration in serum is higher than normal level, the FcRns on the surface of endothelial cells are saturated, and thus cannot bind to more IgG, thereby enhancing IgG degradation and decreasing IgG concentration in serum. By binding FcRn to Fc to protect the Fc-containing protein from being degraded, the high fusion protein concentration in serum can be maintained in a dynamic balance, thereby extending its in vivo half-life.

The present invention, by means of the unique metabolic pathway of immunoglobulin IgG with slow clearance, use a method of fusing a human GLP-1 polypeptide with an Fc section of the human immunoglobulin IgG2 for expression to produce a fusion protein in which GLP-1 has an in vivo half-life close to that of IgG, while maintaining its biological activity.

The fusion protein can be absorbed by subcutaneous injection, and can be administered once every 1 to 2 weeks by subcutaneous injection and maintained an effective in vivo blood drug concentration for a long time due to its prolonged in vivo half-life (the Fc section of IgG2 type having a longer in vivo half-life than those of IgG4 and IgG1 types) (Nature Biotechnology. 2007, 25(12): 1369-1372). Thus, this fusion protein relieves the patients from the pain regarding frequent injections, improves the therapeutic compliance, and reduces the treatment cost.

Although this approach is feasible for GLP-1 therapy, an antibody would be generated when a fusion protein is administered repeatedly over a prolonged period. Furthermore, in view of the fact that the patients with diabetes have to receive treatment during their lifetime after final diagnosis, if the Fc section of the GLP-1-Fc fusion protein retains undesirable effector function, the resultant GLP-1-Fc fusion protein therapy may have a safety concern. The present invention attempts to overcome the problems of potential immunogenicity and effector activity associated with the use of a GLP-1-Fc fusion protein. The fusion protein of the present invention has various amino acid residue substitutions in both the GLP-1 section and the Fc section. The substitutions provide greater potential to increase in vivo stability, reduce immunogenicity and eliminate effector function.

CONTENTS OF THE INVENTION

The present invention provides a recombinant fusion protein in which the amino acid sequence of positions 7 to 37 of a human glucagon-like peptide-1 (GLP-1) is fused with an Fc section of the human immunoglobulin subtype IgG2, and the preparation method and use thereof, wherein the GLP-1 comprises a C-terminus linked to the IgG2 Fc section via a glycine (Gly)-rich peptide linker (Gly-Gly-Gly-Gly-Ser-Gly-Gly-Gly-Gly-Gly-Ser, SEQ ID NO: 11). The fusion protein has the biological activity of GLP-1, and also has a significantly extended in vivo half-life. The fusion protein can be used for the treatment and/or prevention of type II diabetes, obesity, and other diseases that can benefit from decreasing serum glucose, suppressing gastrointestinal motility, and emptying or inhibiting food intake.

The present invention constructs a fusion protein in which GLP-1 is fused with an IgG2 Fc section through gene engineering technology. Particularly, the present invention discloses:

1. A fusion protein, which is obtained by fusing the C-terminus of a glucagon-like peptide-1 with the N-terminus of an IgG2 Fc section via a peptide linker, and comprises an amino acid sequence shown in SEQ ID NO: 4, SEQ ID NO: 5 or SEQ ID NO: 6.

2. A gene encoding the fusion protein described under item 1. In one embodiment, the gene comprises a nucleotide sequence shown in SEQ ID NO: 1, SEQ ID NO: 2 or SEQ ID NO: 3.

3. A method for preparing the fusion protein described under item 1, comprising:
   a) constructing the gene described under item 2;
   b) cloning the gene obtained in step a) into a eukaryotic expression vector, to obtain a eukaryotic expression vector that can express the fusion protein described under item 1; and
   c) transfecting cells with the expression vector obtained in step b), to express the recombinant fusion protein, and then isolating and purifying the fusion protein.

4. A formulation, comprising the fusion protein described under item 1 as an active component, and optionally further comprising one or more pharmaceutically acceptable carriers well-known in the art.

5. Use of the fusion protein described under item 1 or a formulation comprising the same, in the manufacture of a medicament for the treatment and/or prevention of type II diabetes, obesity, and other diseases that can benefit from decreasing serum glucose, suppressing gastrointestinal motility, and emptying or suppressing food intake.

In one embodiment, a gene encoding the fusion protein of the present invention is cloned into a eukaryotic expression vector 293.

In one embodiment, FreeStyle 293F cells are transfected with a eukaryotic expression vector comprising the gene which encodes the fusion protein of the present invention, to express the fusion protein of the present invention.

SPECIFIC MODE FOR CARRYING OUT THE INVENTION

Figure 1:
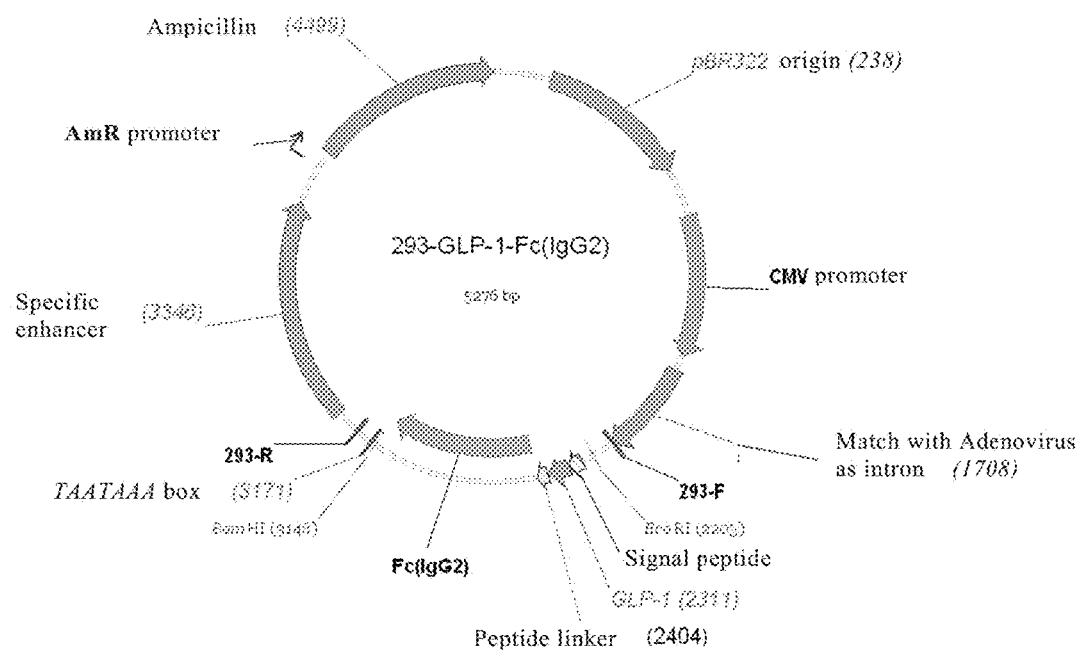
FIG. 1 shows the structure of the recombinant eukaryotic expression vector 293-GLP-1-Fc (IgG2) for expressing the fusion protein of the present invention. Meanwhile, the structures of the recombinant eukaryotic expression vectors for the three fusion proteins of this application, GLP-1-Fc-1, GLP-1-Fc-2 and GLP-1-Fc-3, share the same gene insertion sites.

Unless otherwise indicated, all technical and scientific terms used herein have the same meanings as those generally understood by those skilled in the art to which the present invention pertains.

In one embodiment, the specific technical solution for producing the fusion protein of the present invention is set out as follows:

I. Construction of the Expression Vector Encoding the Fusion Protein of the Present Invention Based on the disclosed GLP-1 (7-37) sequence (Diabetes Metab Res Rev. 2010, 26: 287-296.) and the Fc sequence of IgG2 (AJ250170) disclosed by Pubmed, we synthesized the cDNA sequences which encode a human GLP-1 (7-37), a peptide linker of 15 amino acids, and an IgG2 type Fc section, respectively. The cDNA sequences were used to obtain the fusion gene sequence encoding the fusion protein of the present invention by linking the C-terminus of the gene encoding the human GLP-1 (7-37) to the gene encoding the human IgG2 type Fc section via the peptide linker gene sequence. We made some modifications to the GLP-1 (7-37) amino acid sequence, such that alanine (Ala) at position 8 was replaced with glycine (Gly), glycine (Gly) at position 22 was replaced with glutamic acid (Glu), and arginine (Arg) at position 36 was replaced with glycine (Gly).

The human IgG2 type Fc section in the fusion protein of the present invention has three different modification forms in respect of amino acid sequence, corresponding to three fusion proteins having different sequences which are referred herein as GLP-1-Fc-1, GLP-1-Fc-2 and GLP-1-Fc-3, respectively; the amino acid sequences thereof are shown in SEQ ID NO: 4, SEQ ID NO: 5 and SEQ ID NO: 6, respectively, and the gene sequences thereof are shown in SEQ ID NO: 1, SEQ ID NO: 2 and SEQ ID NO: 3, respectively. In the amino acid sequence (SEQ ID NO: 4) of the GLP-1-Fc-1, it is a secreting signal peptide sequence (the secreting signal peptide refers to the amino acid sequence that generally occurs in the N-terminal region of a large polypeptide, with the functions of initiating the binding of the polypeptide and cellular endoplasmic reticulum, and secreting the polypeptide across plasma membrane) at positions 1-19, a GLP-1 (7-37) sequence at positions 20-50, a peptide linker sequence at positions 51-65, and an IgG2 Fc sequence at positions 66-288 (its hinge region is VECPPCP, SEQ ID NO: 12). In the amino acid sequence (SEQ ID NO: 5) of the GLP-1-Fc-2, it is a signal peptide sequence at positions 1-19, a GLP-1 (7-37) sequence at positions 20-50, a peptide linker sequence at positions 51-65, and an IgG2 Fc sequence at positions 66-292 (its hinge region is ERKCCVECPPCP, SEQ ID NO: 13), and the amino acid K at the C-terminal is deleted). In the amino acid sequence (SEQ ID NO: 6) of the GLP-1-Fc-3, it is a signal peptide sequence at positions 1-19, a GLP-1 (7-37) sequence at positions 20-50, a peptide linker sequence at positions 51-65, and an IgG2 Fc sequence at positions 66-287 (its hinge region is VECPPCP (SEQ ID NO: 12), and the amino acid K at the C-terminal is deleted). In the gene sequence (SEQ ID NO: 1) of the GLP-1-Fc-1, it is a signal peptide gene sequence at positions 1-57, a GLP-1 (7-37) gene sequence at positions 58-150, a peptide linker gene sequence at positions 151-195, and an IgG2 Fc gene sequence at positions 196-864. In the gene sequence (SEQ ID NO: 2) of the GLP-1-Fc-2, it is a signal peptide gene sequence at positions 1-57, a GLP-1 (7-37) gene sequence at positions 58-150, a peptide linker gene sequence at positions 151-195, and an IgG2 Fc gene sequence at positions 196-876. In the gene sequence (SEQ ID NO: 3) of the GLP-1-Fc-3, it is a signal peptide gene sequence at positions 1-57, a GLP-1 (7-37) gene sequence at positions 58-150, a peptide linker gene sequence at positions 151-195, and an IgG2 Fc gene sequence at positions 196-861.

After the three fusion genes encoding the above-mentioned fusion proteins were obtained, molecular cloning technique was employed for further cloning said fusion genes into a eukaryotic expression vector 293 so as to construct the eukaryotic expression vector 293-GLP-1-Fc (IgG2).

For the purpose of the present invention, any suitable eukaryotic expression vector can be used.

II. General Method for Expressing the Fusion Protein of the Present Invention

Eukaryotic host cell FreeStyle 293F was transfected with the expression vector 293-GLP-1-Fc (IgG2) obtained as mentioned above, to generate a fusion protein. The technique for transfecting a host cell using a recombinant DNA is well-known in the art.

III. Collection and Purification of the Recombinant Fusion Protein

The non-antigen binding regions, i.e. the Fc sections, of the three IgG subtypes (IgG1, IgG2 and IgG4), can bind to staphylococci Protein A (SPA), which can be used to purify the antibodies of the above subtypes or the fusion proteins containing the Fc sections of the corresponding subtypes, providing a convenient purification method for the industrial preparation thereof. The Fc-containing fusion protein was obtained by separation and purification through Protein A affinity column. The fusion protein was identified by SDS-PAGE and Western blot.

IV. Assay for In Vitro or In Vivo Activity of the Fusion Protein of the Present Invention 1. Assay for the In Vitro Binding Activity of the Fusion Protein of the Present Invention to Mouse Beta Pancreatic Tumor Cells An assay for the direct binding activity of the fusion protein to GLP-1 receptor (GLP-1R)-positive mouse beta pancreatic tumor cells (β-TC-6) was performed according to the method described in PLoS ONE. 2010, 5 (9): e12734. The results showed that the binding of the fusion protein of the present invention to the GLP-1R on the cells exhibited a specific concentration gradient-dependent increase, suggesting that the GLP-1 fused with the Fc section of the present invention can specifically bind to the corresponding receptor on the cell surface.

2. The Effect of the Fusion Protein of the Present Invention on cAMP Level In Vitro The fusion protein of the present invention was added into β-TC-6 cells, and then the cAMP level was measured according to the method described in Diabetes. 2004, 53: 2492-2500. The results showed that the fusion protein of the present invention resulted in an increase in the cAMP level in vitro with an effect comparable to Liraglutide, suggesting that after binding to the corresponding receptor on the cell surface, the GLP-1 fused with the Fc section of the present invention can activate intracellular signal transmission mediated by the receptor.

3. The effect of the fusion protein of the present invention on insulin secretion level of mouse Beta Pancreatic Tumor Cells In Vitro The fusion protein of the present invention was added into β-TC-6 cells, and then the insulin secretion level of the cells was measured according to the method described in the previous references (Shi-Ying Ding, et al. JBC. 2011, 286 (19): 16768-16774; and PLoS ONE. 2010, 5(9): e12734. The results showed that in the medium with low glucose concentration, the three fusion proteins of the present invention or Liraglutide had no significant promotion effect on insulin secretion of mouse beta pancreatic tumor cells β-TC-6; while in the medium with high glucose concentration, the three fusion proteins at the concentrations of 3, 30, 300 and 1000 nM each can significantly increase the insulin secretion level in β-TC-6 cells to different degrees, with an effect comparable to Liraglutide, and all of them exhibited a concentration gradient-dependent increase.

4. The Effect of the Fusion Protein of the Present Invention on Serum Insulin Level in the Rats Infused with High-Dose Glucose According to the previous references (Diabetes Metab Res Rev. 2010, 26: 287-296; and Diabetes. 2004, 53: 2492-2500), the method that uses normal SD (Sprague-Dawley) rats to establish a high-dose glucose infusion model for measuring the effect of medicaments in promoting increased serum insulin level, is a conventional efficacy assay for detecting the GLP-1-type insulin secretagogues. Said model was used in the present invention, wherein SD rats were injected subcutaneously with the fusion protein of the present invention (3 nM/kg) or Liraglutide (3 nM/kg, as a positive control) or Normal Saline (as a negative control), subjected to overnight fasting (16-18 h), and then sequentially administered the following substances by continuous intravenous infusion: Normal Saline for 20 minutes, low concentration of glucose (50 mg/kg/min) for 30 minutes, and high concentration of glucose (150 mg/kg/min) for 30 minutes. The time point at which Normal Saline infusion is finished was taken as a zero point, and blood samples were collected at minutes −20, 0, 30 and 60, respectively. The results showed that in the healthy rats group administered with Normal Saline by subcutaneous injection, after intravenous infusion with Normal Saline or low concentration of glucose, the serum insulin level has no significant increase compared with the non-intravenous infusion group, while after intravenous infusion with high concentration of glucose, the serum insulin level increases significantly; in the healthy rats group administered with the three fusion proteins of the present invention or Liraglutide by subcutaneous injection, intravenous infusion with Normal Saline still cannot induce any increase in serum insulin level, while after intravenous infusion with low concentration or high concentration of glucose, the serum insulin level increases to different degrees compared with the insulin level induced by glucose infusion of the corresponding concentrations in the group administered with Normal Saline by subcutaneous injection. The effect in the experimental animals for promoting insulin secretion in a glucose concentration-dependent manner suggests that the fusion proteins of the present invention in which the GLP-1 (7-37) is fused with the Fc section can be absorbed through subcutaneous injection, and can exert the same pharmacological effect as Liraglutide.

5. Assay for Binding Ability of the Fusion Protein of the Present Invention to Neonatal Receptor Protein (FcRn)

According to the method described in a previous reference (The Journal of Biological Chemistry. 2001, 276(9): 6591-6604), the fusion protein of the present invention was coated onto an ELISA plate, and the plate was added with an FcRn protein labeled with His and then incubated under acidic condition (pH=6.0). The FcRn bound to the fusion protein was detected by a murine anti-His monoclonal antibody and a goat anti-mouse antibody labeled with horseradish peroxidase (HRP) (goat anti-human IgG-HRP). The results showed that compared with the Fc section of the control antibody of IgG1 type, the Fc section of the fusion protein of the present invention has an FcRn binding ability comparable to that of IgG1. As the endocytosis and circulation of the Fc section-containing protein mediated by FcRn on vascular endothelial cells can maintain the stable state of the protein concentration in serum, the experimental results suggested that the in vivo half-life of the GLP-1-Fc fusion protein may be comparable to the IgG1 antibody, which is far higher than that of Liraglutide (which needs to be injected once a day), and realizes an injection frequency of once every 1 to 2 weeks.

6. Assay for the Effector Activity of the Fusion Protein of the Present Invention According to the method described in the previous references (Angiogenesis. 2004, 7: 335-345; and Cancer Res. 2010: 4481-4489), an FcγRIIIa (CD16a) protein was coated onto an ELISA plate, and the plate was added with the fusion protein of the present invention. The binding ability of the fusion protein to the FcγRIIIa (CD16a) protein was detected. The results showed that compared with the Fc section of the control antibody of IgG1 type, the Fc section of the fusion protein of the present invention exhibited very low binding to the FcγRIIIa (CD16a) protein, thereby avoiding the effector function (such as ADCC) of the Fc section.

As mentioned above, the assay results of in vitro and in vivo biological activity show that the three fusion proteins of the present invention not only have normal biological activity of GLP-1 (7-37) polypeptide, but also possess significantly longer biological half-life than GLP-1 (7-37) polypeptide; and since the effector function of the Fc section thereof is weak, the effector function that is not associated with the treatment purpose will not be induced such that the application of the medicament is more safe.

The advantageous effects of the present invention are as follows: the GLP-1 (7-37) the fusion protein maintains the natural function; the human IgG2 type Fc section extends the half-life and facilitates the purification of the fusion protein; and the effector function that is not associated with the treatment is avoided.

The reasons why the fusion protein of the present invention has an extended half-life are as follows:

1) The GLP-1 (7-37) section is modified by replacing alanine (Ala) at position 8 with glycine (Gly), which can reduce the degradation of the fusion protein by DPP-4, thereby extending the half-life thereof; and 2) The Fc section of the fusion protein can bind to FcRn, thereby making the half-life of the fusion protein be comparable to those of the IgG1 and IgG2 antibodies.

The following examples are included to describe how to implement the embodiments of the present invention. These examples are intended to illustrate the present invention, but not to limit the protection scope of the present invention in any manner.

Example 1: Construction of the Expression Vector Encoding the Fusion Protein of the Present Invention The gene (SEQ ID NO: 1) encoding the GLP-1-Fc-1 fusion protein of the present invention was synthesized and cloned into pGEM-T plasmid vector by Shanghai Generay Biotech Co., Ltd. The gene contains EcoR I, Not I and Hind III enzyme cutting sites at 5' end, and TGA termination codon and Pme I, Xho I, and BamH I enzyme cutting sites at 3' end. The pGEM-T plasmid vector was designated as GLP-1-Fc-1-T.

Figure 2:
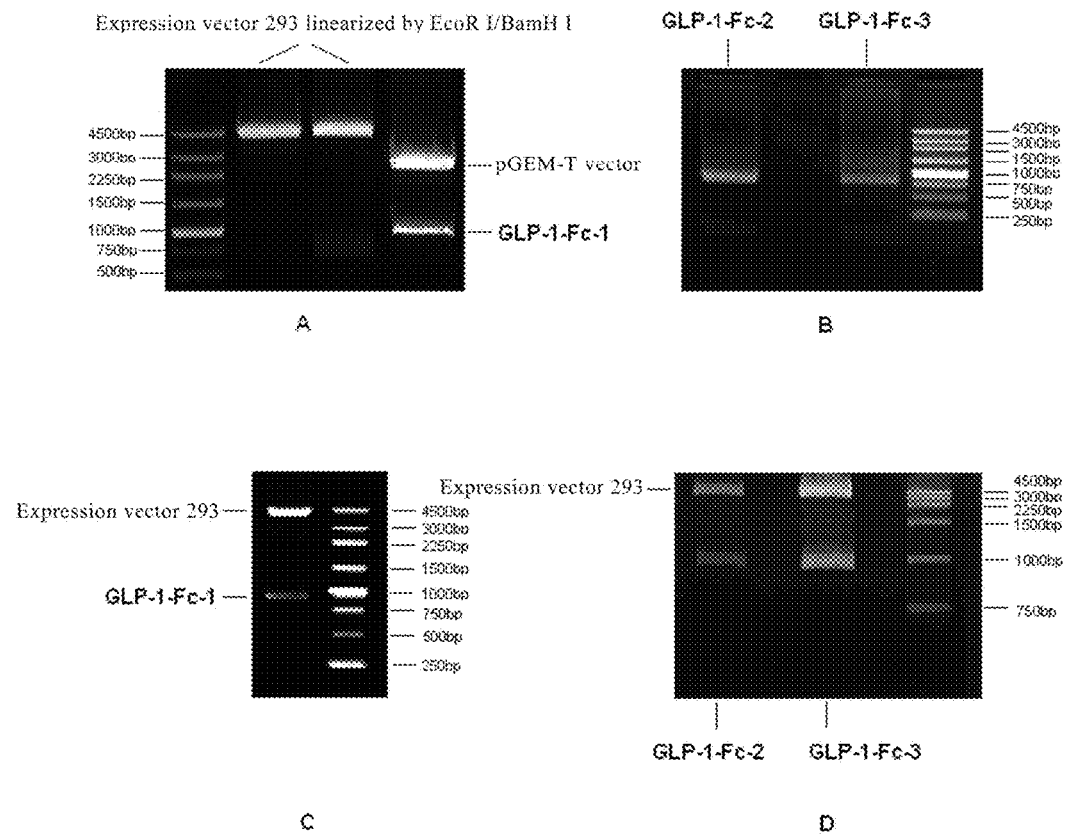
FIG. 2A shows the DNA agarose electropherograms of the fragment obtained by double digesting and linearizing the expression vector 293 with the enzymes EcoR I and BamH I, and of the gene fragment that encodes the fusion protein GLP-1-Fc-1 obtained by enzyme digestion of pGEM-T plasmid vector (synthesized by Generay™).
FIG. 2B shows the gene fragments encoding the fusion proteins GLP-1-Fc-2 and GLP-1-Fc-3 obtained by polymerase chain reaction (PCR).
FIGS. 2C and 2D respectively show DNA agarose electropherograms for identifying the constructed expression vectors 293 encoding the three fusion proteins by double digested with enzymes EcoR I and BamH I.

The plasmid vector GLP-1-Fc-1-T was double digested with enzymes EcoR I and BamH I (purchased from NEB Co.) (37° C., 4 hours) according to the instruction. 1% agarose gel electrophoresis (FIG. 2A) showed that a gene fragment encoding the GLP-1-Fc-1 fusion protein with a length of about 950 bp, and a pGEM-T plasmid vector fragment with a length of about 3000 bp were generated after double enzymatic digestion. GLP-1-Fc-1 gene fragment was extracted by a gel extraction kit according to the instruction (the gel extraction kit is purchased from Axygen Co.). Meanwhile, an expression vector 293 (FreeStyle MAX293 Expression System, K900-20, purchased from Invitrogen Co.) was double digested with enzymes EcoR I and BamH I (37° C. 4 hours). FIG. 2A shows the presence of a 293-EcoR I/BamH I fragment with a length of about 4300 bp after double enzymatic digestion. Said fragment was recovered by the above gel extraction kit.

The above two gene fragments GLP-1-Fc-1 and 293-EcoR I/BamH I obtained from enzymatic digestion were ligated via T4 DNA ligase (purchased from NEB Co.) (16° C., 16 hours). The ligation product was transformed into *E. coli* by heat shock (42° C., 90 seconds), and plated (Amp$^+$ LB medium, i.e. Amp$^+$-resistant Luria-Bertani medium). The resultant clones were picked and used to extract the plasmids. The plasmids were double digested with the enzymes EcoR I/BamH I (37° C., 2 hours) for identification and screening. Positive clones obtained by screening contain the successfully constructed eukaryotic expression vector 293-GLP-1-Fc-1 (as shown in FIG. 2C).

Polymerase chain reaction (PCR) was performed using GLP-1-Fc-1-T plasmid as a template and the primers 1, 2, 3 and 4, so as to give two intermediate products of the corresponding gene GLP-1-Fc-2. Subsequently, overlap-PCR was performed using the two intermediate products as the templates and the primers 1 and 4, so as to give a gene fragment GLP-1-Fc-2.

Polymerase chain reaction (PCR) was performed using GLP-1-Fc-1-T plasmid as the template and the primers 1 and 4, so as to give a gene fragment GLP-1-Fc-3.

PCR primers are set out as follows:

1.
(SEQ ID NO: 7)
5'-GCGGCCGCGAATTCATGGAGTTGGGACTGTCTTG-3';

2.
(SEQ ID NO: 8)
5'-CCACCGCCACCGTCGCTCGCGTTTACAACACAGCTC-3';

3.
(SEQ ID NO: 9)
5'-GGTGCCGCTGGCAGCGAGCGCAAATGTTGTGTCGAGTGC-3';
and 4.
(SEQ ID NO: 10)
5'-GTTTAAACGGATCCTCAACCCGGAGACAGGGAGAG-3'.

FIG. 2B shows the gene fragments encoding the fusion proteins GLP-1-Fc-2 and GLP-1-Fc-3 both with a length of about 950 bp. The gene fragments GLP-1-Fc-2 and GLP-1-Fc-3 were recovered by the above-mentioned method, double digested with enzymes EcoR I and BamH I (37° C., 4 hours), and ligated to 293-EcoR I/BamH I fragment obtained by double digested with enzymes EcoR I and BamH I (37° C., 4 hours) via T4 DNA ligase (16° C., 16 hours). The ligation product was transformed into *E. coli* by heat shock (42° C., 90 seconds), and plated (Amp$^+$ LB medium). The resultant clones were picked and used to extract the plasmids. The plasmids were double digested with enzymes EcoR I/BamH I (37° C., 2 hours) for identification and screening. Positive clones obtained by screening contain the successfully constructed eukaryotic expression vectors 293-GLP-1-Fc-1 and 293-GLP-1-Fc-3 (as shown in FIG. 2D).

FIG. 1 is a gene structure diagram of the successfully constructed expression vector 293-GLP-1-Fc (IgG2). The three expression vectors 293-GLP-1-Fc-1, 293-GLP-1-Fc-2 and 293-GLP-1-Fc-3 have substantially the same gene structure, except that their genes of about 950 bp between the enzyme cutting sites of EcoR I and BamH I respectively encode GLP-1-Fc-1, GLP-1-Fc-2 and GLP-1-Fc-3 fusion proteins, which respectively have the nucleotide sequences shown in SEQ ID NO: 1. SEQ ID NO: 2 and SEQ ID NO: 3, and the amino acid sequences shown in SEQ ID NO: 4, SEQ ID NO: 5 and SEQ ID NO: 6. FIGS. 2C and 2D are the identification results of the eukaryotic expression vectors 293-GLP-1-Fc-1, 293-GLP-1-Fc-2 and 293-GLP-1-Fc-3 by double digestion with enzymes EcoR I/BamH I, showing that they have correct fusion protein gene fragments and 293-EcoR I/BamH I fragments respectively having a length of about 950 bp and 4300 bp.

Example 2: Expression of the Fusion Protein of the Present Invention

The expression of the recombinant expression vectors 293-GLP-1-Fc-1, 293-GLP-1-Fc-2 and 293-GLP-1-Fc-3 constructed in Example 1 can be carried out by the method of transiently transfecting FreeStyle 293F cells (R790-07, purchased from Invitrogen Co.). 24 hours prior to transfection, FreeStyle 293F cells were subcultured at a concentration of $6 \times 10^5$ cells/ml, and cultured in a constant temperature shaker at 135 rpm under the condition of 37° C. and 8% $CO_2$, such that the cell density is about $1.2-1.5 \times 10^6$ cells/ml on the day of transfection. The cells were diluted with the FreeStyle 293F culture medium (12338-018, purchased from Invitrogen Co.) to the density of $1 \times 10^6$ cells/ml. To ensure the optimal transfection effect, the cell viability should be more than 95%.

The transfection agent FreeStyle Max Reagent (16447-500, purchased from Invitrogen Co.) was mixed well by gentle reverse mixing for 4 times. 625 μg of 293-GLP-1-Fc-1, 293-GLP-1-Fc-2 and 293-GLP-1-Fc-3 vector plasmids were added respectively to the transfection nutrient solution OptiPRO SFM (12309-050, purchased from Invitrogen Co.), and the mixture was further supplemented with OptiPRO SFM to reach a volume of 10 ml and mixed well. In another centrifuge tube, 625 μl of the FreeStyle Max Reagent was diluted with OptiPRO SFM to the volume of 10 ml, and mixed well by gentle reverse mixing. The diluted plasmid and the diluted FreeStyle Max Reagent were mixed well and incubated at room temperature for 15 minutes. 20 ml of the mixed solution was added slowly to a shake flask containing 500 ml FreeStyle 293F culture medium. The shake flask was incubated in a constant temperature shaker 135 rpm for 7 days (37° C. and 8% $CO_2$).

After 7 days, the cells respectively expressing the three fusion proteins of GLP-1-Fc-1, GLP-1-Fc-2 and GLP-1-Fc-3 were centrifuged at 9,000 rpm for 20 minutes in a refrigerated centrifuge. The supernate was harvested for the subsequent protein purification.

Example 3: Purification of the Fusion Protein of the Present Invention

The supernates of the FreeStyle 293F cells respectively containing the three fusion proteins of the present invention obtained in the above Example 2 were applied to a Protein A column (71-5000-09 AD, purchased from GE Healthcare Bio-Sciences Co.) on an AKTA instrument (purchased from GE Healthcare Bio-Sciences Co.), to capture the three fusion proteins, respectively. The three fusion proteins were eluted with 50 mM citric acid-sodium citrate buffer (pH=3.3) to collect the eluates, respectively (each about 0.5 ml); and 100 μl of 1 M tris(hydroxymethyl)aminomethane-hydrochloric acid (Tris-HCL) buffer (pH=11.0) was added to neutralize the eluates to be neutral. The protein contents were determined at OD280 nm respectively, and then the proteins were dialyzed against phosphate buffer PBS (0.01M $Na_2HPO_4.12H_2O$+0.002M $KH_2PO_4P$+0.14M NaCl+0.002M KCl, PH=7.2) through a 10 K dialysis membrane, filtered and sterilized through a 0.22 μm filter (purchased from Millipore Co.), and stored at −80° C.

Figure 3:
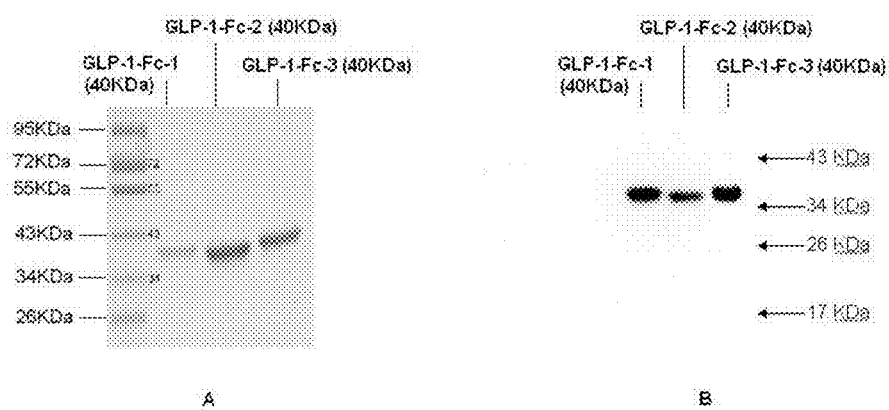
FIG. 3A shows polyacrylamide gel electropherograms (SDS-PAGE) of the three fusion proteins.
FIG. 3B is a graph showing the western blot results of the three fusion proteins.

Example 4: SDS-PAGE and Western-Blot of the Fusion Protein of the Present Invention 10% polyacrylamide gel electrophoresis was used to determine the purity and the molecular weight of the purified three fusion proteins which have been reduced by 50 mM of DTT (DL-dithiothreitol); and Western blot was used to further identify the property and the molecular weight thereof. The resultant electrophoresis gel is transferred onto PVDF (polyvinylidene fluoride) membrane via an electrotransfer method (300 mA, 80 minutes). After the membrane was blocked with 10% skimmed milk, 1 μg/ml mouse anti-human GLP-1 (7-37) monoclonal antibody (purchased from BioPorto Co.) was added. The membrane was incubated at 4° C. overnight, and washed with PBST (PBS buffer containing 0.02% Tween-20) twice. Goat anti-mouse IgG (H+L) antibody labeled with HRP (1 μg/ml, purchased from R&D Co.) was added. The membrane was washed again with PBST twice after incubating at room temperature for 45 minutes, and finally treated by electrochemiluminescence (ECL) method for color development. The results of polyacrylamide gel electrophoresis (FIG. 3A) and Western blot (FIG. 3B) both show that under reduction conditions, all of the three fusion proteins GLP-1-Fc-1. GLP-1-Fc-2 and GLP-1-Fc-3 have a band with a molecular weight of about 40 KDa, being consistent with the theoretical molecular weight thereof. These results demonstrated that the three fusion proteins constructed by the present invention have correct structures and properties.

Example 5: Assay for In Vitro Binding Activity of the Fusion Protein of the Present Invention to the β-TC-6 Cells $8.5 \times 10^6$ of mouse beta pancreatic tumor cells β-TC-6 (purchased from ATCC) were collected, centrifuged and fixed with 8.5 ml of fixative (IC Fixation buffer, purchased from Invitrogen Co.) (4° C., 10 min). The resultant cells were centrifuged again, resuspended with 3.4 ml of PBS, and seeded at a density of $2.5 \times 10^5$ cells/well (100 μl) in a 96-well U-shaped plate. In the meantime, the three fusion proteins of the present invention were diluted 4-fold with PBS starting from 500 μg/ml to obtain a total of 10 gradients, respectively.

The cells in the 96-well U-shaped plate were centrifuged and the supernate was removed. The diluted fusion proteins were added at 100 μl/well into the plate, and then the plate was incubated at 4° C. for 1 hour. The cells were centrifuged again to remove the supernate, and washed with 200 μl/well of PBS twice. 1 μg/ml (100 μl/well) of goat anti-human antibody IgG labeled with HRP (purchased from Bethyl laboratories Co.) was added, and then the plate was incubated at 4° C. for 45 minutes. After centrifugation, the cells were washed with 200 μl/well of PBS for three times. 100 μl/well of color developing solution (9 ml of substrate buffer+1 ml of substrate color developing solution+10 μl of 0.3% $H_2O_2$ solution, wherein the substrate buffer is 0.02 M citric acid+0.01 M $Na_2HPO_4.12H_2O$, and the substrate color developing solution is 2 mg/ml of TMB, i.e. 3,3',5,5'-tetramethyl benzidine) were added. The plate was incubated at room temperature for color development for 15 minutes, and then 50 μl/well of stop buffer (1 M sulfuric acid) was added. The absorbance at a wavelength of 450/570 nm was read on a M5 multifunctional microplate reader (purchased from Molecular Devices Co.), and the results are shown in FIG. 4.

Figure 4:
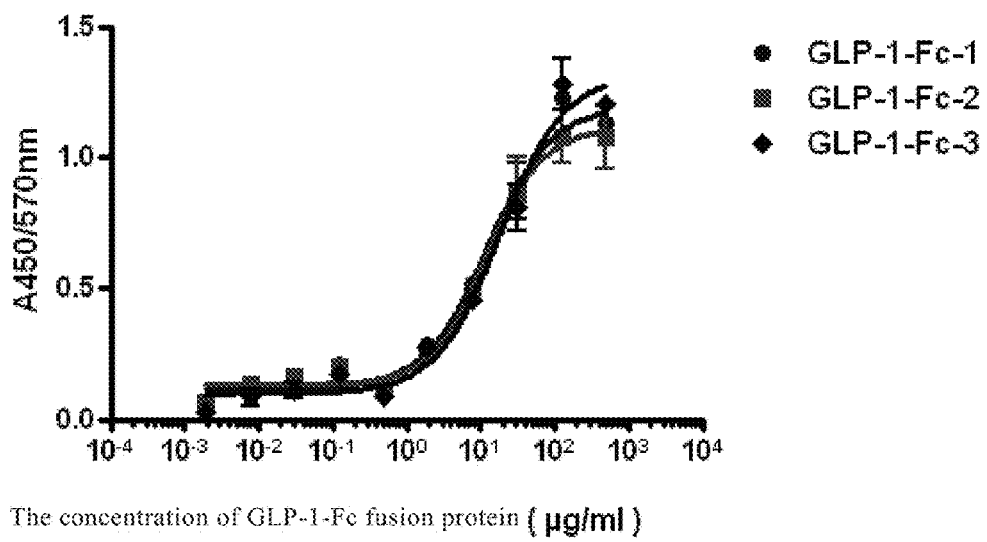
FIG. 4 is a graph showing the experimental results of the binding of the three fusion proteins on β-TC-6 cells.

As shown in FIG. 4, all of the three fusion proteins GLP-1-Fc-1, GLP-1-Fc-2 and GLP-1-Fc-3 of the present invention show a specific binding activity to GLP-1R on the surface of β-TC-6 cells.

Example 6: The Effect of the Fusion Protein of the Present Invention on cAMP Level in β-TC-6 Cells In Vitro The β-TC-6 cells were seeded at a density of $1\times10^4$ cells/well (5 μl/well, DMEM medium without serum and glucose, purchased from Gibco Co.) into a 384-well plate, to which 5 μl/well of 5000 μM cAMP inhibitor IBMX (3-isobutyl-1-methylxanthine, purchased from Sigma Co.) in DMEM medium without serum and glucose was added such that the final concentration of IBMX is 2500 μM. The cells were starved in an incubator at 37° C. for 4 to 5 hours.

The 384-well plate was centrifuged 800 rpm for 1 minute. After the supernate was removed at 5 μl/well, 250 mM glucose and 25 mM IBMX were added each at 1 μl/well, and then the three fusion proteins of the present invention and the control medicament Liraglutide (purchased from Novo Nordisk Co.) were added each at 1 μl/well, such that the three fusion proteins and Liraglutide all have four different final concentrations of 2, 10, 50 and 250 nM. Either non-protein group or Liraglutide group (0 nM) is used as control. Finally, DMEM medium without serum and glucose was added at 1 μl/well, and the resultant mixture was mixed well by gently shaking the 384-well plate, and reacted at room temperature for 30 minutes.

A control curve and a standard curve were established according to the experimental procedures in the cAMP detection kit (Dynamic2 Kit, purchased from Cisbio Co.). The values were read on a M5 multifunctional microplate reader (Flu668/620 nm), and the results are shown in FIG. 5.

Figure 5:
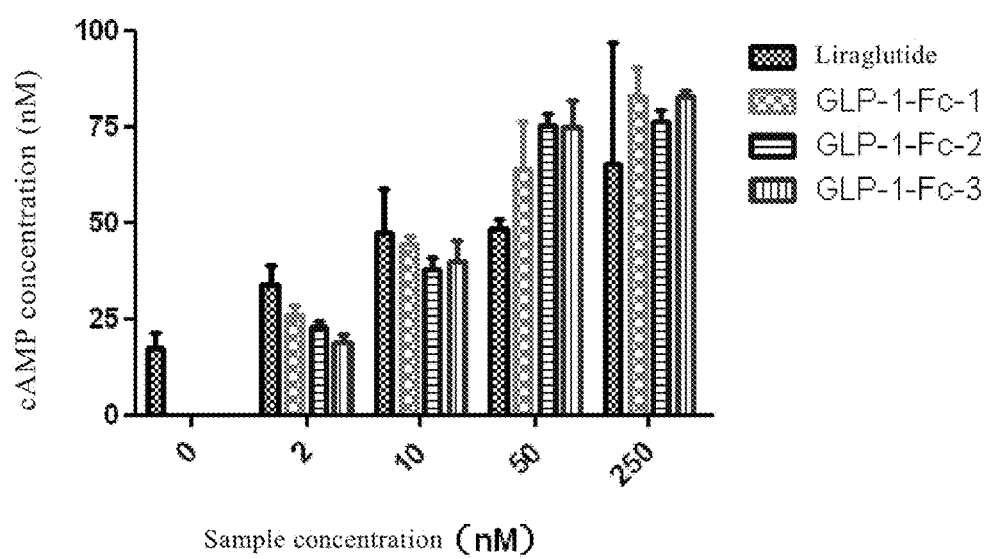
FIG. 5 is a graph showing the experimental results that the three fusion proteins could promote cAMP (adenosine 3',5'-cyclic monophosphate) release in β-TC-6 cells.

The results of FIG. 5 show that the three fusion proteins of the present invention at different concentrations can increase the cAMP level in mouse beta pancreatic tumor cells β-TC-6 in vitro to different degrees, and their effects are equivalent to that of Liraglutide, all showing a concentration gradient-dependent increase. The results suggest that after binding to the corresponding receptor on the cell surface, the GLP-1 fused with the Fc section can activate the intracellular signal transmission mediated by the receptor.

Example 7: The Effect of the Fusion Protein of the Present Invention on Insulin Secretion Level in β-TC-6 Cells In Vitro The β-TC-6 cells grown on DMEM medium containing 10% FBS (fetal bovine serum, purchased from Gibco Co.) were seeded at a density of $2.5\times10^5$ cells/well (500 μl) into a 24-well plate and cultured at 37° C. overnight. The supernate was removed. The cells were washed once with Krebs-Ringer Buffer (KRB buffer, 125 mM NaCl+5.9 mM KCl+1.28 mM $CaCl_2$+1.2 mM $MgCl_2$+25 mM HEPES+ 0.1% BSA, pH7.4), added with the KRB buffer again, and starved at 37° C. for 2 hours. The supernate was removed. The three fusion proteins and the control medicament Liraglutide at different concentrations were added, such that the four samples all have final concentrations of 0, 3, 30, 300 and 1000 nM (the diluents are KRB buffer+16.8 mM glucose). The low glucose concentration group without the four samples (containing KRB buffer+2.8 mM glucose) is used as a negative control group (neg). The reaction was carried out at 37° C. for 1 hour.

A control curve and a standard curve were established according to the experimental procedures in the insulin detection kit (Insulin Kit, purchased from Cisbio Co.). The insulin standard has an initial concentration of 20 ng/ml, and diluted into 7 gradients by two-fold dilution. In the meantime, the samples (the cell supernates) were diluted to 0-20 ng/ml (being diluted 10-fold) with KRB buffer. To a 384-well plate, the KRB buffer, the diluted standard and the diluted samples were added, each 10 μl. Two fluorescence-labeled antibodies, anti-insulin Ab-cryptate and anti-insulin Ab-XL665, were further added, each 5 μl/well (both of them are from Insulin Kit, purchased from Cisbio Co.). The resultant mixture was mixed well by gently shaking the 384-well plate and incubated at room temperature for 2 hours. The values were read on a M5 multifunctional microplate reader (wavelength 1: excitation/emission=314 nm/668 nm; wavelength 2: excitation/emission=314 nm/620 nm).

The data were processed as follows: Ratio=A668 nm/A620 nm×104; Deta F=(standard ratio or sample ratio−KRB ratio)/KRB ratio; a standard curve was plotted; and the insulin value of the sample was calculated.

Figure 6:
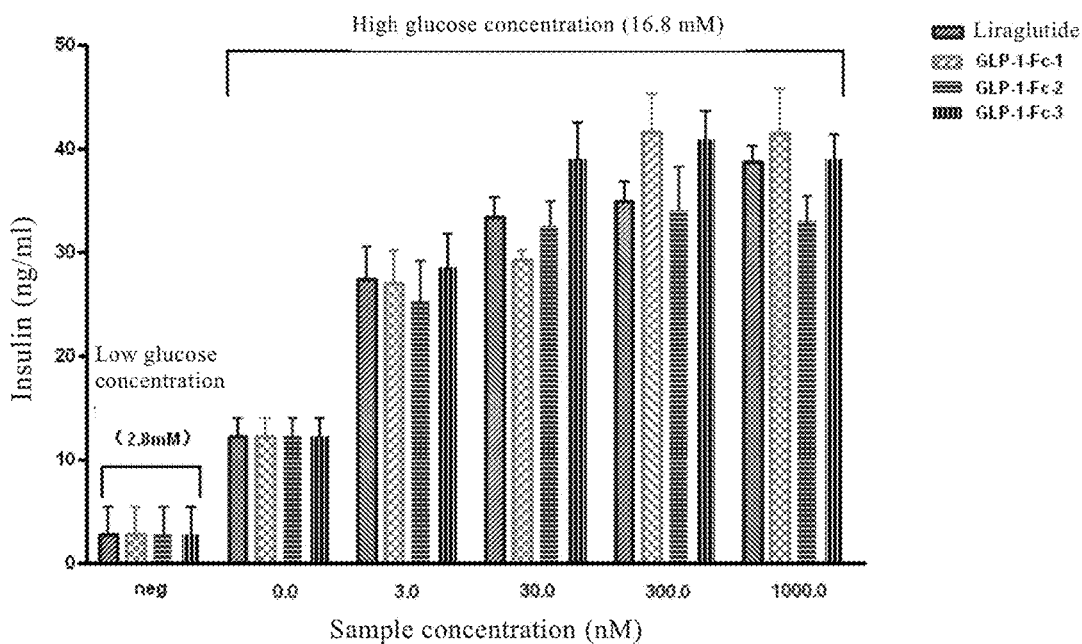
FIG. 6 is a graph showing the experimental results that the three fusion proteins could promote insulin secretion in β-TC-6 cells.

The results of FIG. 6 show that in in-vitro normal cell medium (results not shown) or in the medium containing low concentration (2.8 mM) of glucose (neg), the three fusion proteins of the present invention or Liraglutide have no significant promotion effect on insulin secretion in mouse beta pancreatic tumor cells β-TC-6 (used as a control); while in the medium containing high concentration (16.8 mM) of glucose, the negative control group containing no sample (0.0) has somewhat increased promotion effect on insulin secretion in β-TC-6 cells, and the three fusion proteins at the concentrations of 3, 30, 300 and 1000 nM each can significantly increase insulin secretion level in β-TC-6 cells to different degrees, and their effects are comparable to Liraglutide, all showing a concentration gradient-dependent increase. The results suggest that the final effect of the GLP-1 fused with the Fc section resulted from activating the corresponding receptor on the cell surface is to promote insulin secretion in a glucose concentration-dependent manner.

Example 8: The Effect of the Fusion Protein of the Present Invention on Serum Insulin Level in the Rats Infused with High-Dose Glucose SD (Sprague-Dawley) rats were injected subcutaneously with the three fusion proteins of the present invention (3 nM/kg) or Liraglutide (3 nM/kg) or Normal Saline (as a negative control), subjected to overnight fasting, and then sequentially administered the following substances by continuous intravenous infusion (16-18 h): Normal Saline for 20 minutes, low concentration of glucose (50 mg/kg/min) for 30 minutes, and high concentration of glucose (150 mg/kg/min) for 30 minutes. The time point at which Normal Saline infusion is finished was taken as a zero point, and blood samples were collected at −20, 0, 30 and 60 min, respectively. The blood samples were centrifuged at 4000 rpm for 10 minutes to isolate the serum. The insulin level in serum was measured by the method described in the previous references (Diabetes Metab Res Rev. 2010, 26: 287-296: and Diabetes. 2004, 53: 2492-2500).

Figure 7A:
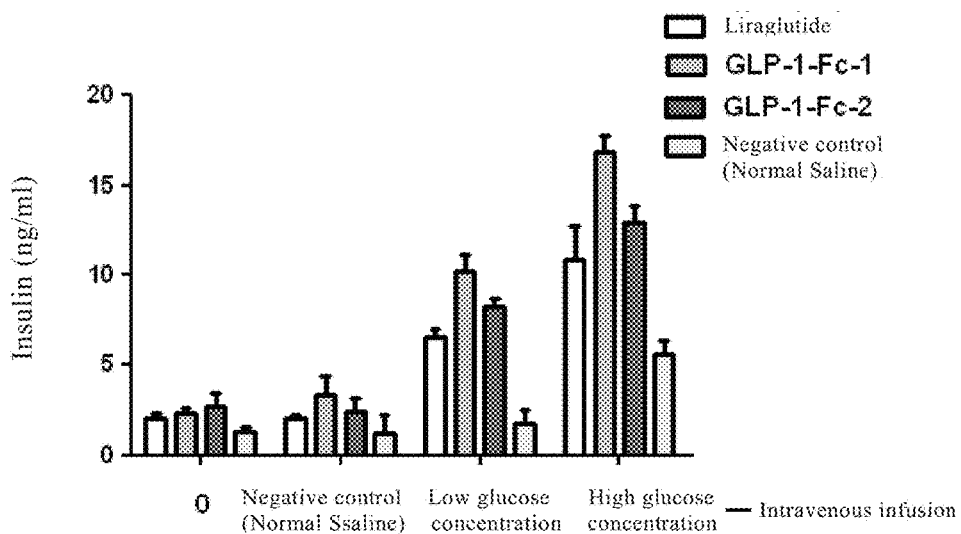
FIGS. 7A and 7B are graphs showing the experimental results that the three fusion proteins could improve serum insulin level in a rat model of high-dose glucose infusion, respectively.
Figure 7B:
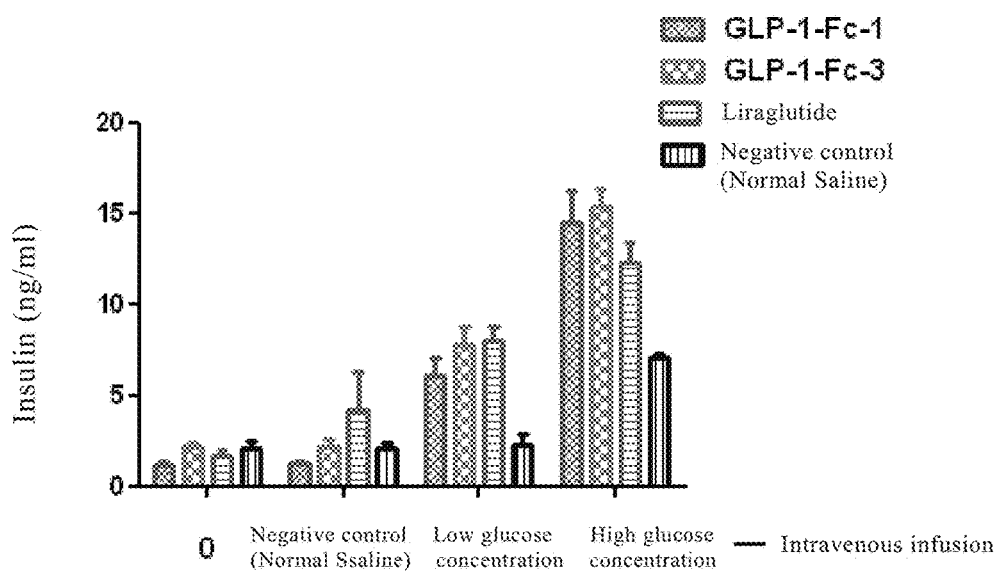

The results in FIGS. 7A and 7B show that in the healthy rats group administered with Normal Saline by subcutaneous injection (the negative control group), after intravenous infusion with Normal Saline or low concentration of glucose, the serum insulin level has no significant increase compared with the non-intravenous infusion group, while after intravenous infusion with high concentration of glucose, the serum insulin level increases significantly; in the healthy rats group administered with the three fusion proteins of the present invention or Liraglutide by subcutaneous injection, intravenous infusion with Normal Saline still cannot induce any increase in serum insulin level, while after intravenous infusions with low concentration or high concentration of glucose, the serum insulin level increases to different degrees compared with the insulin level induced by glucose infusion of the corresponding concentrations in the group administered with Normal Saline by subcutaneous injection. The effect in experimental animal for promoting insulin secretion in a glucose concentration-dependent manner suggests that the fusion proteins of the present invention can be absorbed through subcutaneous injection, and can exert the same pharmacological effect as Liraglutide.

Example 9: Assay for Binding Ability of the Fusion Protein of the Present Invention to FcRn The three fusion proteins of the present invention and a control IgG1 antibody (Remicade, purchased from Xi'an Janssen Pharmaceutical Ltd.) were respectively diluted to 5 μg/ml with PBS, and then added to an ELISA plate at 100 μl/well. The plate was coated at 4° C. overnight. After washing with PBST for 4 times, the plate was added with 1% BSA (Bovine Serum Albumin) at 300 μl/well, and then blocked at room temperature for 1 hour. An FcRn protein (purchased from Sino Biological Co.) was diluted into 7 gradients by two-fold dilution starting from 5 μg/ml. After the plate was washed with PBST (pH=6.0) for 4 times, the above FcRn protein was added at 100 μl/well into the ELISA plate, and the plate was incubated at room temperature for 1 hour under acidic condition (pH=6.0). After the plate was washed with PBST (pH=6.0) for 4 times, a murine anti-His monoclonal antibody (purchased from R&D Co.) was diluted to 1 μg/ml with PBS buffer and added at 100 μl/well to the ELISA plate, and the plate was incubated at room temperature for 1 hour. After the plate was washed with PBST (pH=6.0) for 4 times, a goat anti-mouse antibody labeled with HRP (goat anti-mouse IgG-HRP, purchased from R&D Co.) was diluted to 1 μg/ml with PBS buffer and added at 100 μl/well to the ELISA plate, and the plate was incubated at room temperature for 1 hour. After the plate was washed with PBST (pH=6.0) for 4 times, TMB color developing solution was added to the plate at 100 μl/well, and the plate was incubated at room temperature for 15 minutes. After color development, a stop buffer was added at 50 μl/well. The absorbance at a wavelength of 450/570 nm was read on a M5 multifunctional microplate reader, and the results are shown in FIG. 8.

Figure 8:
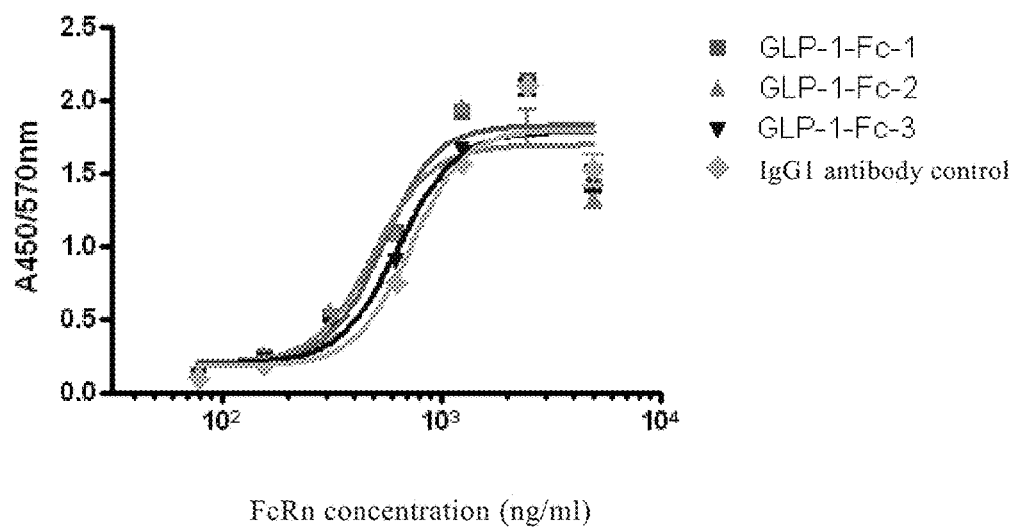
FIG. 8 is a graph showing the experimental results of the binding between the three fusion proteins and FcRn protein.

The results in FIG. 8 show that the Fc sections of the fusion proteins of the present invention all have an FcRn binding ability comparable to the Fc section of control antibody of IgG1 type. As the endocytosis and circulation of the Fc section-containing protein mediated by FcRn on vascular endothelial cells can maintain the stable state of the protein concentration in serum, the experimental results suggest that the in vive half-life of the GLP-1-Fc fusion protein may be comparable to the antibody of IgG1 type, which is far higher than that of Liraglutide (which needs to be injected once a day), and realizes an injection frequency of once every 1-2 weeks.

Example 10: Assay for Effector Activity of the Fc Section of the Fusion Protein of the Present Invention An FcγRIIIa (CD16a) protein (purchased from Sino Biological Co.) was diluted to 0.25 μg/ml with PBS buffer, and added to an ELISA plate at 100 μl/well. The plate was coated at 4° C. overnight. After washing with PBST for 4 times, the plate was added with 1% BSA at 300 μl/well, and then blocked at room temperature for 1 hour. The three fusion proteins of the present invention and a control antibody of IgG1 type (Herceptin, purchased from Roche Co.) were diluted into 7 gradients by 4-fold dilution starting from 200 μg/ml, and a rabbit anti-human κchain antibody (purchased from R&D Co.) was diluted into 7 gradients by 4-fold dilution starting from 100 μg/ml. Then, each fusion protein dilution was mixed well with a rabbit anti-human κchain antibody dilution in a ratio of 1:1, and the mixtures were incubated at room temperature for 1 hour. After washing with PBST for 4 times, the ELISA plate coated with FcγRIIIa (CD16a) protein was added with the incubated mixtures at 100 μl/well, and incubated at room temperature for 2 hours. After washing with PBST for 4 times, the plate was added with 1 μg/ml F(ab')$_2$ antibody fragment of the goat anti-human IgG H&L chain labeled with HRP (goat anti-human IgG H&L chain F(ab')$_2$ fragment-HRP, purchased from CalBiochem Co.) diluted with PBS at 100 μl/well, and incubated at room temperature for 1 hour. After washing with PBST for 4 times, the plate was added with TMB color developing solution at 100 μl/well, and incubated at room temperature for 15 minutes for color development. After color development, a stop buffer was added at 50 μl/well. The absorbance at a wave length of 450/570 nm was read on a M5 multifunctional microplate reader, and the results are shown in FIG. 9.

Figure 9:
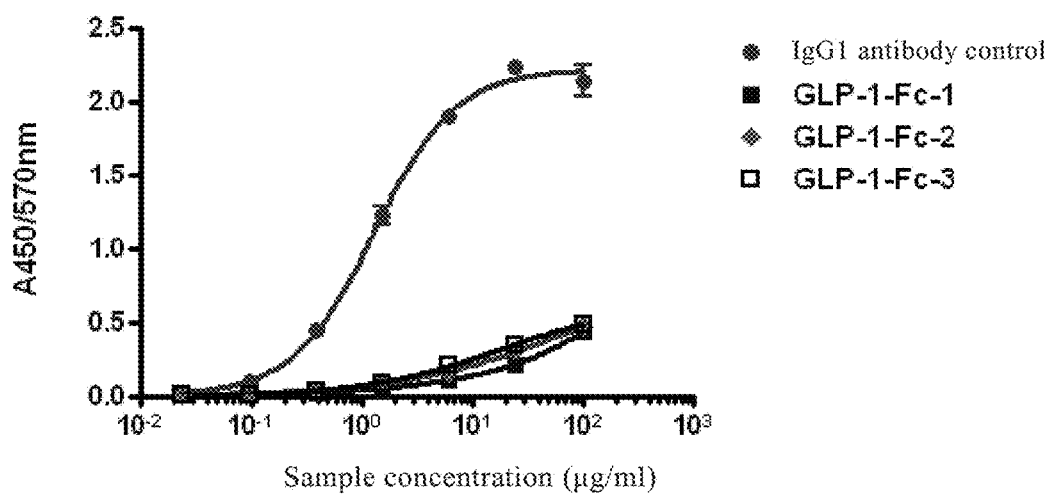
FIG. 9 is a graph showing the experimental results of the binding between the three fusion proteins and FcγRIIIa (CD16a) protein.

The results in FIG. 9 show that compared with the Fc section of the control antibody of IgG1 type, the Fc sections of the three fusion proteins of the present invention exhibit very low binding to FcγRIIIa (CD16a) protein, thereby avoiding the effector function (such as ADCC) of the Fc section thereof and minimizing the side effects of the medicaments.

---

The invention claimed is:

1. A fusion protein obtained by fusing the C-terminus of a glucagon-like peptide-1 with the N-terminus of an IgG2 Fc section via a peptide linker, wherein the fusion protein comprises a sequence from amino acid position 20 to amino acid position 288 as shown in SEQ ID NO: 4.

2. The fusion protein according to claim 1, comprising an amino acid sequence shown in SEQ ID NO: 4, SEQ ID NO: 5 or SEQ ID NO: 6.

3. A gene encoding the fusion protein according to claim 2.

4. The gene according to claim 3, comprising a nucleotide sequence shown in SEQ ID NO: 1, SEQ ID NO: 2 or SEQ ID NO: 3.

5. A method for preparing the fusion protein according to claim 2, comprising:
    a) constructing a gene encoding the fusion protein according to claim 2;
    b) cloning the gene obtained in step a) into a eukaryotic expression vector, to obtain a eukaryotic expression vector that can express the fusion protein according to claim 2; and
    c) using the expression vector obtained in step b) to transfect cells to express the recombinant fusion protein in the cells, and then isolating and purifying the fusion protein.

6. The method according to claim 5, wherein the eukaryotic expression vector is the eukaryotic expression vector 293.

7. The method according to claim 5, wherein the cells to be used are FreeStyle 293F cells.

8. A formulation, comprising the fusion protein according to claim 2 as an active component, and optionally further comprising one or more pharmaceutically acceptable carriers.

9. A gene encoding the fusion protein according to claim 1.

10. The gene according to claim 9, comprising a nucleotide sequence shown in SEQ ID NO: 1, SEQ ID NO: 2 or SEQ ID NO: 3.

11. A method for preparing the fusion protein according to claim 1, comprising:
    a) constructing a gene encoding the fusion protein according to claim 1;
    b) cloning the gene obtained in step a) into a eukaryotic expression vector, to obtain a eukaryotic expression vector that can express the fusion protein according to claim 1; and
    c) using the expression vector obtained in step b) to transfect cells to express the recombinant fusion protein in the cells, and then isolating and purifying the fusion protein.

12. The method according to claim 11, wherein the eukaryotic expression vector is the eukaryotic expression vector 293.

13. The method according to claim 11, wherein the cells to be used are FreeStyle 293F cells.

14. A formulation, comprising the fusion protein according to claim 1 as an active component, and optionally further comprising one or more pharmaceutically acceptable carriers.

* * * * *